(12) United States Patent
Shin et al.

(10) Patent No.: US 8,323,229 B2
(45) Date of Patent: Dec. 4, 2012

(54) BALLOON TYPE STENT SYSTEM FOR TREATMENT OF OBESITY

(75) Inventors: Kyong-Min Shin, Seoul (KR); Yong-Hyun Won, Incheon-si (KR)

(73) Assignees: Taewoong Medical Co., Ltd., Kyunggi-do (KR); Kyong-Min Shin, Seoul (KR)

( * ) Notice: Subject to any disclaimer, the term of this patent is extended or adjusted under 35 U.S.C. 154(b) by 287 days.

(21) Appl. No.: 12/892,991

(22) Filed: Sep. 29, 2010

(65) Prior Publication Data

US 2011/0082535 A1 Apr. 7, 2011

(30) Foreign Application Priority Data

Oct. 1, 2009 (KR) .................. 10-2009-0093700

(51) Int. Cl.
*A61F 2/04* (2006.01)

(52) U.S. Cl. ... 604/8; 623/23.64; 623/23.65; 623/23.67; 606/153; 606/192

(58) Field of Classification Search .............. 604/8, 9; 606/153, 192; 623/1.15, 23.64, 23.65, 23.66, 623/23.67, 23.68, 23.7

See application file for complete search history.

(56) References Cited

U.S. PATENT DOCUMENTS

2007/0100367 A1* 5/2007 Quijano et al. ............... 606/192
2011/0004320 A1* 1/2011 Priplata et al. ............. 623/23.65

* cited by examiner

*Primary Examiner* — Tatyana Zalukaeva
*Assistant Examiner* — Benjamin Klein
(74) *Attorney, Agent, or Firm* — IP & T Group LLP

(57) ABSTRACT

A balloon type stent system for treatment of obesity is disclosed. An injection expansion unit and a plurality of distribution expansion units extend in a longitudinal direction of a stent unit body formed by coupling two sheets of synthetic vinyl in the shape of a cylinder. The injection expansion unit has an expansion agent injection port, and the distribution expansion units each have a distribution injection port communicating with a distribution channel. Connection ends are partially cut in the longitudinal direction such that the expansion units are divided into an integrated expansion unit and a separated expansion unit. The injection expansion unit and the distribution expansion units constituting the separated expansion unit are bent outward to form a balloon type stent unit. A tube has a length corresponding to a lumen length of the duodenum, and the tube is connected to the stent unit body by a connection wire.

6 Claims, 18 Drawing Sheets

BALLOON TYPE STENT SYSTEM FOR TREATMENT OF OBESITY

CROSS-REFERENCE TO RELATED APPLICATION

The Present Application claims priority of Korean Patent Application No. 10-2009-0093700, filed on Oct. 1, 2009, which is incorporated herein by reference in its entirety.

BACKGROUND OF THE INVENTION

1. Field of the Invention

The present invention relates to a balloon type stent system for treatment of obesity, and, more particularly, to a balloon type stent system for treatment of obesity that is capable of preventing food from being converted into nutritive substances by bile and thus preventing the nutritive substances from being absorbed into a body of an obese patient, thereby lowering a degree of obesity of the obese patient.

2. Description of the Related Art

Generally, a body weight of a human divided by a square of height (kg/m2) is referred to as a body mass index. From a medical point of view, East Asians having a body mass index of 30 or more may be regarded as being obese.

For East Asians, visceral fat percentage, abdominal fat percentage, and body fat percentage are fully examined together with such simple weight so as to finally diagnose obesity.

Obesity may have a negative influence upon human health. Also, obesity abruptly increases a possibility of occurrence of diabetes, high blood pressure, high blood cholesterol, fatty liver, etc., which are typical complications of obesity.

An attack rate of such diseases has suddenly increased, and, correspondingly, a death rate due to such diseases has suddenly increased.

Obese people are very unlikely to achieve weight loss through diet and exercise and to keep it off for a long period of time as compared with overweight people.

According to statistics, obese patients frequently attempt more excessive and extreme weight loss programs than overweight people, with the result that a probability of occurrence of a yo-yo phenomenon is outstandingly increased.

In a case in which such obese patients have personal histories in which conservative treatment methods, such as diet, exercise, and correction of behaviors and habits have failed, in a case in which such obese patients have a body mass index of 30 or more and suffer from diabetes, high blood pressure, high blood cholesterol, fatty liver, arthritis, sleep apnea, etc., which result from obesity, and in a case in which such obese patients have a body mass index of 35 or more, i.e., super obesity, the obese patients may be classified as morbid obesity or abdominal obesity, which is a typical form of obesity for East Asians, and are candidates for surgical operations.

For example, stomach stapling, one of such surgical operations, may be used. In the stomach stapling, a large curved part of the stomach, at which the size of the stomach is increased, is cut along a curved line of a small curved part of the stomach excluding the antrum of the stomach, which performs a digestive function, to form the stomach in the shape of a tube.

After such stomach stapling is performed with respect to an obese patient, the obese patient may quickly feel full after eating only a small amount of food. As a result, the amount of food that the obese patient eats is reduced, thereby preventing overeating and binge eating. Although the obese patient has a compulsion to eat before a surgical operation, the obese patient has normal desire to eat after the surgical operation.

However, such stomach stapling requires hospital treatment or outpatient treatment after the surgical operation, which is very inconvenient. Also, the stomach stapling may cause vomiting, diarrhea, hernia, abdominal infection, pneumonia, respiratory diseases. Furthermore, a digestive fluid may leak from the stomach due to poor connection between the stomach and the small intestine.

In addition, medical expenses related to the above diseases may be increased. For example, an additional burden of expenses due to complications may occur in addition to expenses necessary to perform a surgical operation for obesity treatment and to perform six-month follow-up treatment after the surgical operation.

SUMMARY OF THE INVENTION

Therefore, the present invention has been made in view of the above problems, and it is an object of the present invention to provide a balloon type stent system for treatment of obesity that is capable of enabling food digested in the stomach of an obese patient to pass through the duodenum of the obese patient along a tube, so as to prevent the food from being converted into nutritive substances through enzymatic decomposition caused by bile in the duodenum and thus prevent the nutritive substances from being absorbed by the duodenum, thereby lowering a degree of obesity of the obese patient and thus effectively treating obesity of the obese patient.

It is another object of the present invention to provide a balloon type stent system for treatment of obesity configured such that a doughnut type expansion unit is inserted into the body of the stomach, thereby enabling the obese patient to feel full.

It is a further object of the present invention to provide a balloon type stent system for treatment of obesity configured such that a plurality of doughnut type expansion units are provided, and one of the doughnut type expansion units positioned at the center of the body of the stomach has the largest diameter, thereby achieving smooth movement of the food digested in the stomach.

In accordance with the present invention, the above and other objects can be accomplished by the provision of a balloon type stent system for treatment of obesity configured such that an injection expansion unit and a plurality of distribution expansion units extend in a longitudinal direction of a stent unit body formed by coupling two sheets of synthetic vinyl in the shape of a cylinder, the injection expansion unit and a plurality of distribution expansion units are divided uniformly along a circumference of the stent unit body, the injection expansion unit has an expansion agent injection port formed at one end thereof, and the distribution expansion units each have a distribution injection port communicating with a distribution channel formed in a circumferential direction of the stent unit body such that the distribution channel communicates with the other end of the injection expansion unit opposite to the end of the injection expansion unit at which the expansion agent injection port is formed in a longitudinal direction of the injection expansion unit, such that connection ends interconnecting the injection expansion unit and the distribution expansion units formed at the stent unit body are partially cut in a longitudinal direction such that the expansion units are divided into an integrated expansion unit and a separated expansion unit, the injection expansion unit and the distribution expansion units constituting the separated expansion unit are bent outward to form a balloon type stent unit, and such that a tube is formed in the shape of a cylinder which is flexible and thin, the tube has a length corresponding to a length of a lumen of a duodenum of an obese patient having the balloon type stent system for treatment of obesity inserted therein, and the tube is connected to a lower end of the stent unit body at a side where the integrated expansion unit of the balloon type stent unit is formed by a connection wire.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
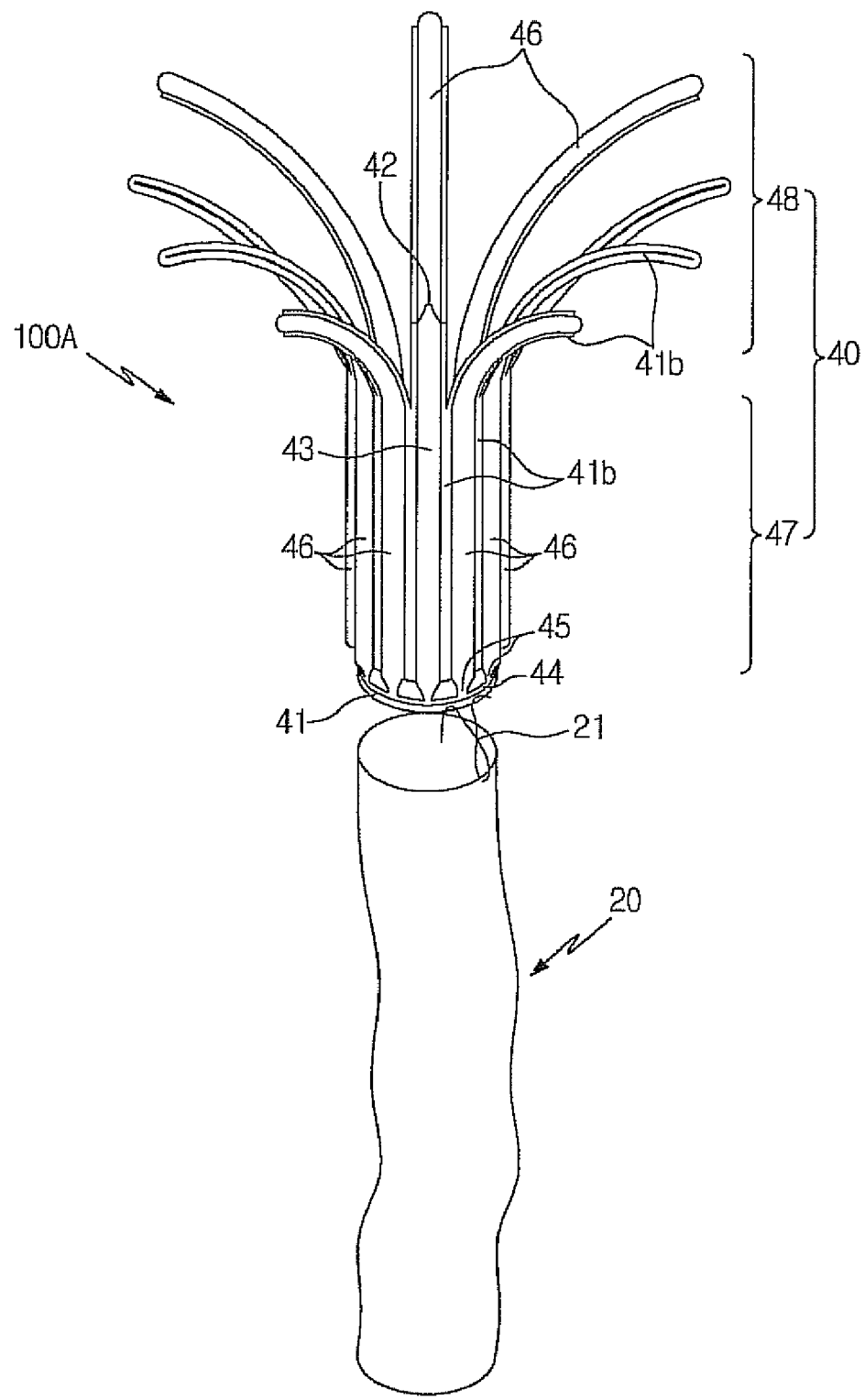
FIG. 1 is an exploded perspective view illustrating a balloon type stent system for treatment of obesity including a balloon type stent unit and a tube according to an embodiment of the present invention.
Figure 2:
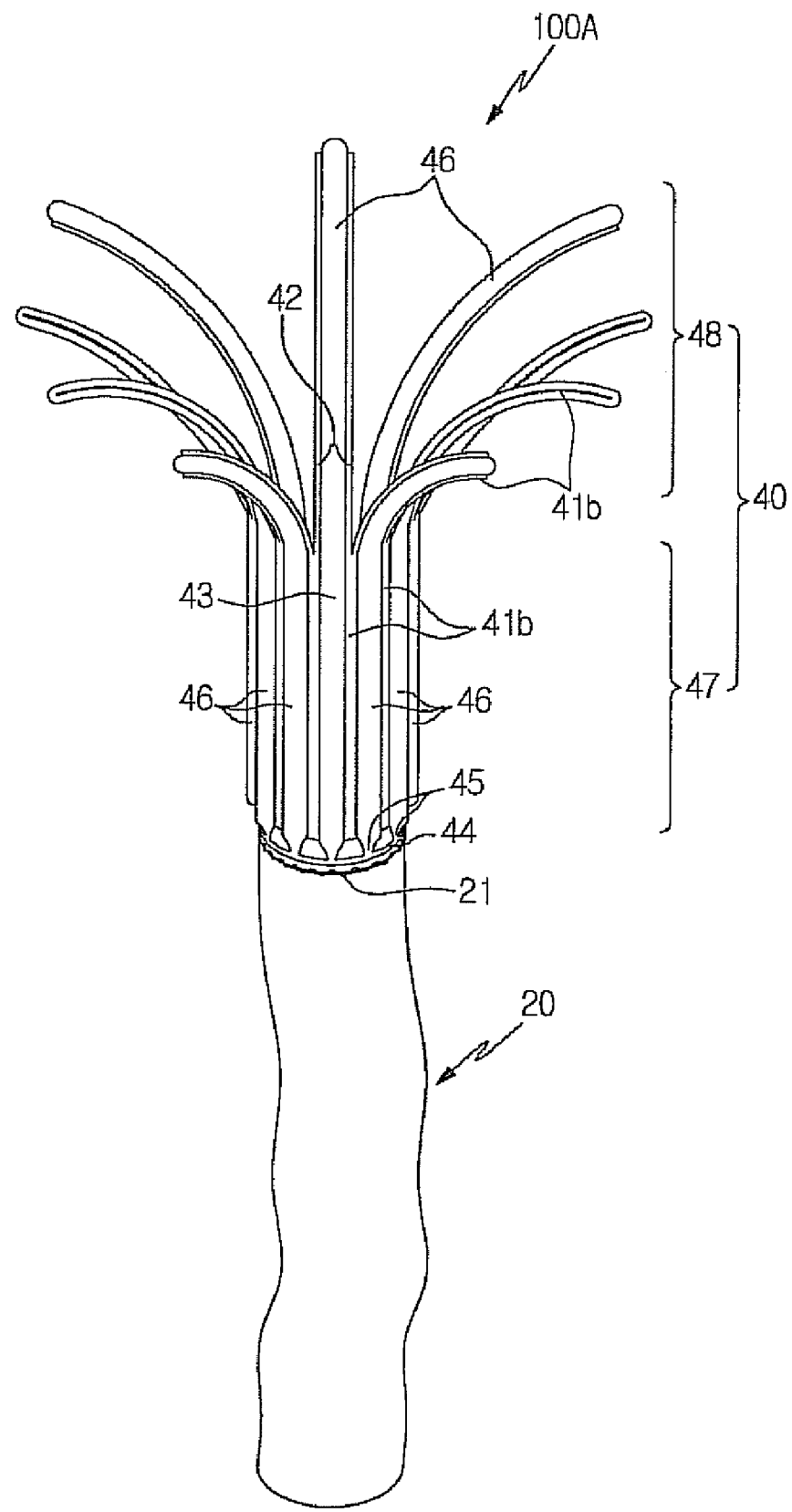
FIG. 2 is an assembled perspective view of FIG. 1.
Figure 3A:
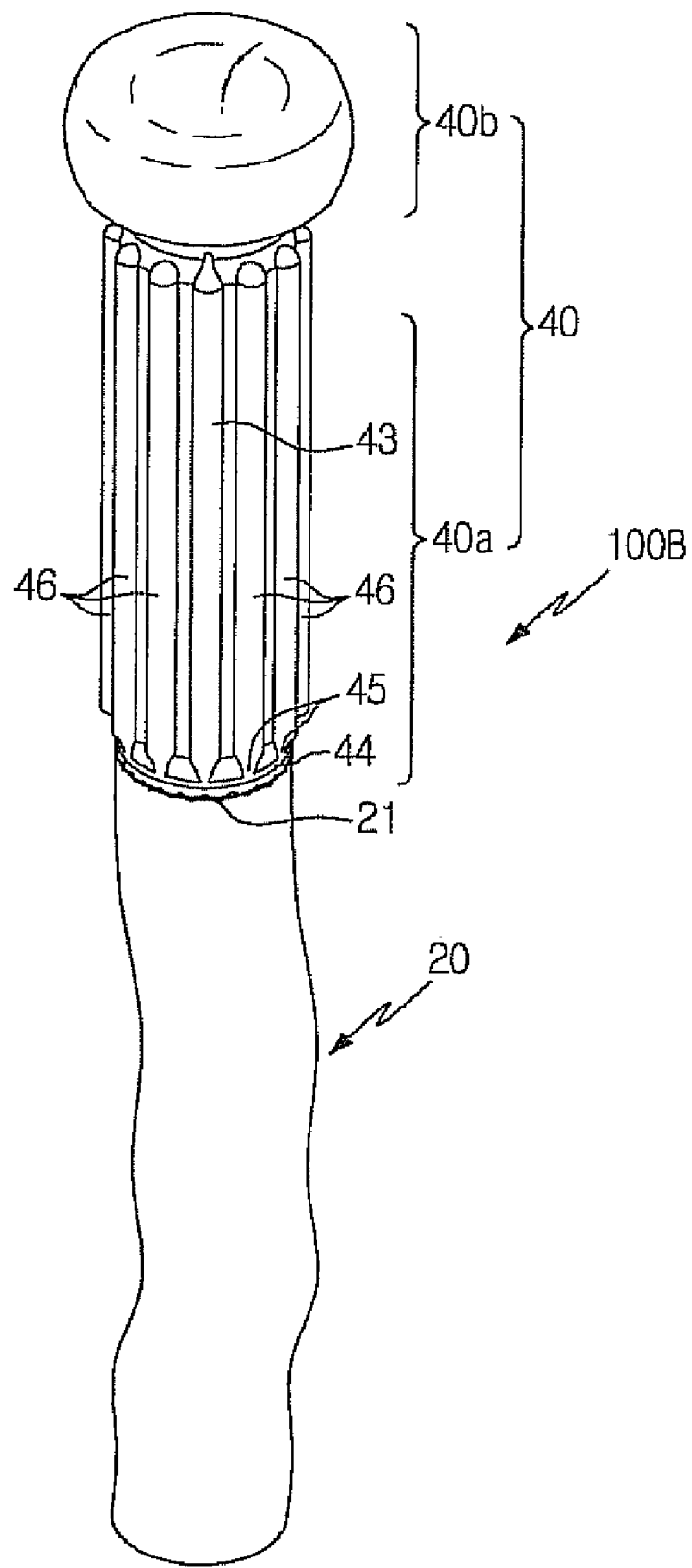
FIG. 3A is a perspective view illustrating a balloon type stent system for treatment of obesity according to another embodiment of the present invention.
Figure 3B:
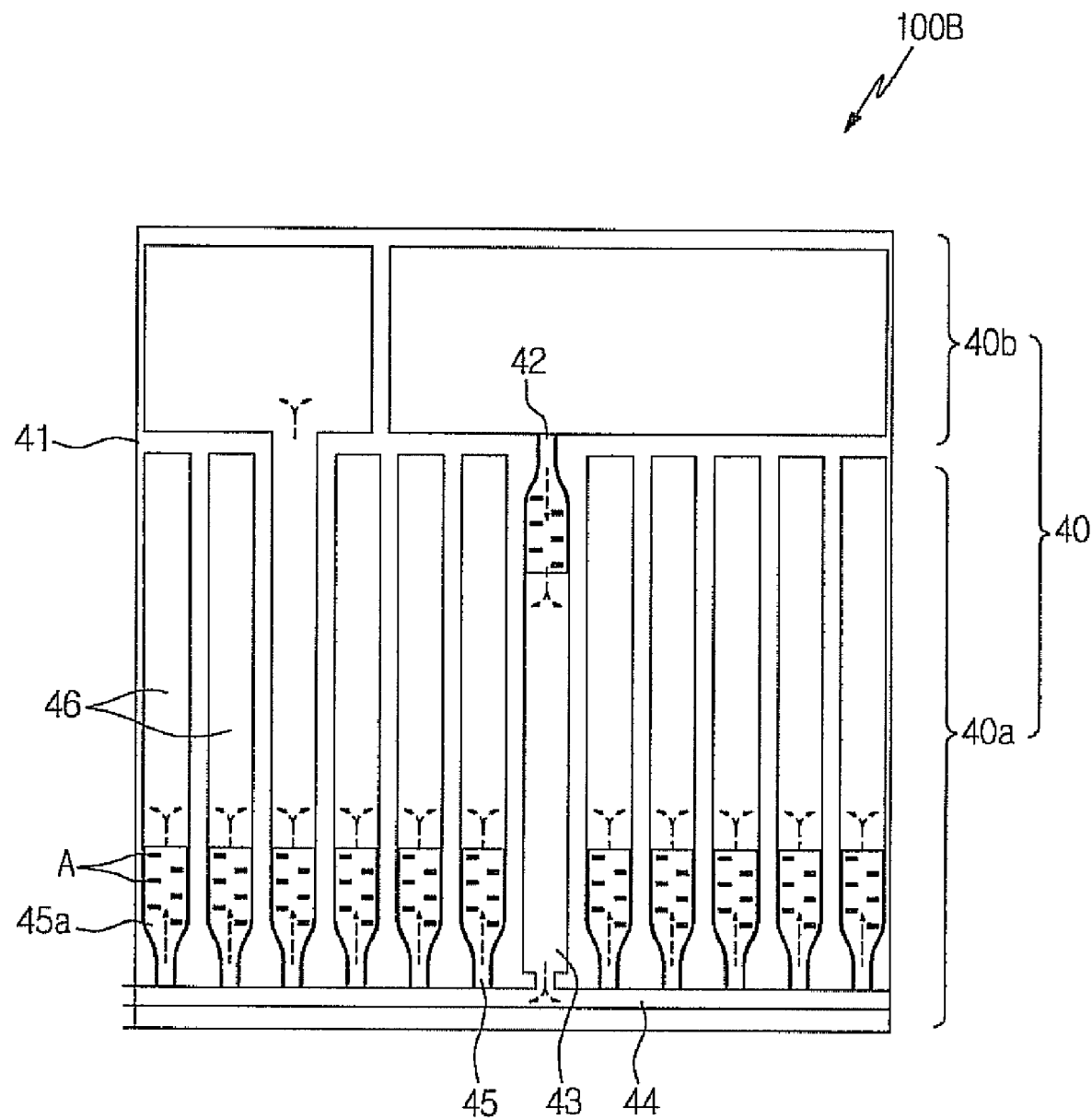
FIG. 3B is a development view of FIG. 3A.

Now, preferred embodiments of the present invention will be described in detail with reference to the accompanying drawings.

Based on shape, a balloon type stent system for treatment of obesity according to the present invention is classified into two kinds. One kind of the balloon type stent system for treatment of obesity is an obesity prevention stent system 100A including a balloon type stent unit 40, a portion of which is formed in the shape of a cylinder and a portion of which is bent outward in a spreading state, and a tube 20 connected to the balloon type stent unit 40, as shown in FIGS. 1, 2 and 6 to 7G. The other kind of the balloon type stent system for treatment of obesity is an obesity prevention stent system 100B including a balloon type stent unit 40, a portion of which is formed in the shape of a cylinder and a portion of which is formed in the shape of a doughnut, and a tube 20 connected to the balloon type stent unit 40.

As shown in FIGS. 1, 2 and 6 to 7G, the balloon type stent unit 40 of the obesity prevention stent system 100A includes a stent unit body 41, which is formed by coupling two sheets of synthetic vinyl 41a in the shape of a cylinder.

The stent unit body 41 is provided with an injection expansion unit 43 and a plurality of distribution expansion units 46, which extend in the longitudinal direction of the stent unit body 41 and which are divided uniformly along the circumference of the stent unit body 41.

The injection expansion unit 43 has an expansion agent injection port 42.

The distribution expansion units 46 each have a distribution injection port 45 communicating with a distribution channel 44 formed in the circumferential direction of the stent unit body 41 such that the distribution channel 44 communicates with the end of the injection expansion unit 43 opposite to the end of the injection expansion unit 43 at which the expansion agent injection port 42 is formed in the longitudinal direction of the injection expansion unit 43.

Connection ends 41b interconnecting the injection expansion unit 43 and the distribution expansion units 46 formed at the stent unit body 41 are partially cut in the longitudinal direction.

As a result of partial cutting as described above, the expansion units are divided into an integrated expansion unit 47 and a separated expansion unit 48.

The injection expansion unit 43 and the distribution expansion units 46 constituting the separated expansion unit 48 are bent outward.

The expansion agent injection port 42 is formed at the injection expansion unit 43 of the separated expansion unit 48.

The tube 20 is formed in the shape of a cylinder which is flexible and thin. The tube 20 has a length corresponding to the length of the lumen of the duodenum 300. The tube 20 is connected to the lower end of the stent unit body 41 at the side where the integrated expansion unit 47 of the balloon type stent unit 40 is formed. The tube 20 is connected to the lower end of the stent unit body 41 by a connection wire 21.

The injection expansion unit 43 and the distribution expansion units 46 of the balloon type stent unit 40 have expansion spaces 42d and 45d communicating with the expansion injection port 42 and the distribution injection ports 45, respectively. The injection expansion unit 43 and the distribution expansion units 46 of the balloon type stent unit 40 are formed in the shape of a bottle.

Also, ends of expansion agent discharge prevention films 42a and 45a, formed in the shape of a bottle, at which each of the expansion agent discharge prevention films 42a and 45a has a small area is attached to inner walls of the expansion injection port 42 and the distribution injection ports 45 so as to form injection spaces 42b and 45b.

On the other hand, ends of the expansion agent discharge prevention films 42a and 45a at which each of the expansion agent discharge prevention films 42a and 45a has a large area are locally attached, through thermal binding A, to inner walls of the expansion spaces 42d and 45d opposite to the sides at which the small area ends of the expansion agent discharge prevention films 42a and 45a are attached so as to form filling spaces 42c and 45c.

That is, when the expansion agent is injected through the injection spaces 42b and 45b, the filling spaces 42c and 45c are filled with the expansion agent. As a result, the expansion agent discharge prevention films 42a and 45a are pressed by the expansion agent. Consequently, the injection spaces 42b and 45b are closed, and the expansion agent discharge prevention films 42a and 45a come into tight contact with the inner walls of the expansion spaces 42d and 45d to prevent discharge of the expansion agent.

As shown in FIGS. 3A, 3B, and 6 to 7G, the balloon type stent unit 40 of the obesity prevention stent system 100B includes a stent unit body 41, which is formed by coupling two sheets of synthetic vinyl 41a in the shape of a cylinder.

The stent unit body 41 is provided with an injection expansion unit 43 and a plurality of distribution expansion units 46, which extend in the longitudinal direction of the stent unit body 41 and which are divided uniformly along the circumference of the stent unit body 41.

The injection expansion unit 43 has an expansion agent injection port 42.

The distribution expansion units 46 each have a distribution injection port 45 communicating with a distribution channel 44 formed in the circumferential direction of the stent unit body 41 such that the distribution channel 44 communicates with the end of the injection expansion unit 43 opposite to the end of the injection expansion unit 43 at which the expansion agent injection port 42 is formed in the longitudinal direction of the injection expansion unit 43. The injection expansion unit 43 and the distribution expansion units 46 constitute a cylindrical expansion unit 40a.

A doughnut type expansion unit 40b, which is configured to expand in the shape of a doughnut upon expansion of the doughnut type expansion unit 40b, is connected to the stent unit body 41 of the cylindrical expansion unit 40a. The doughnut type expansion unit 40b communicates with one of the distribution expansion units 46.

Figure 4A:
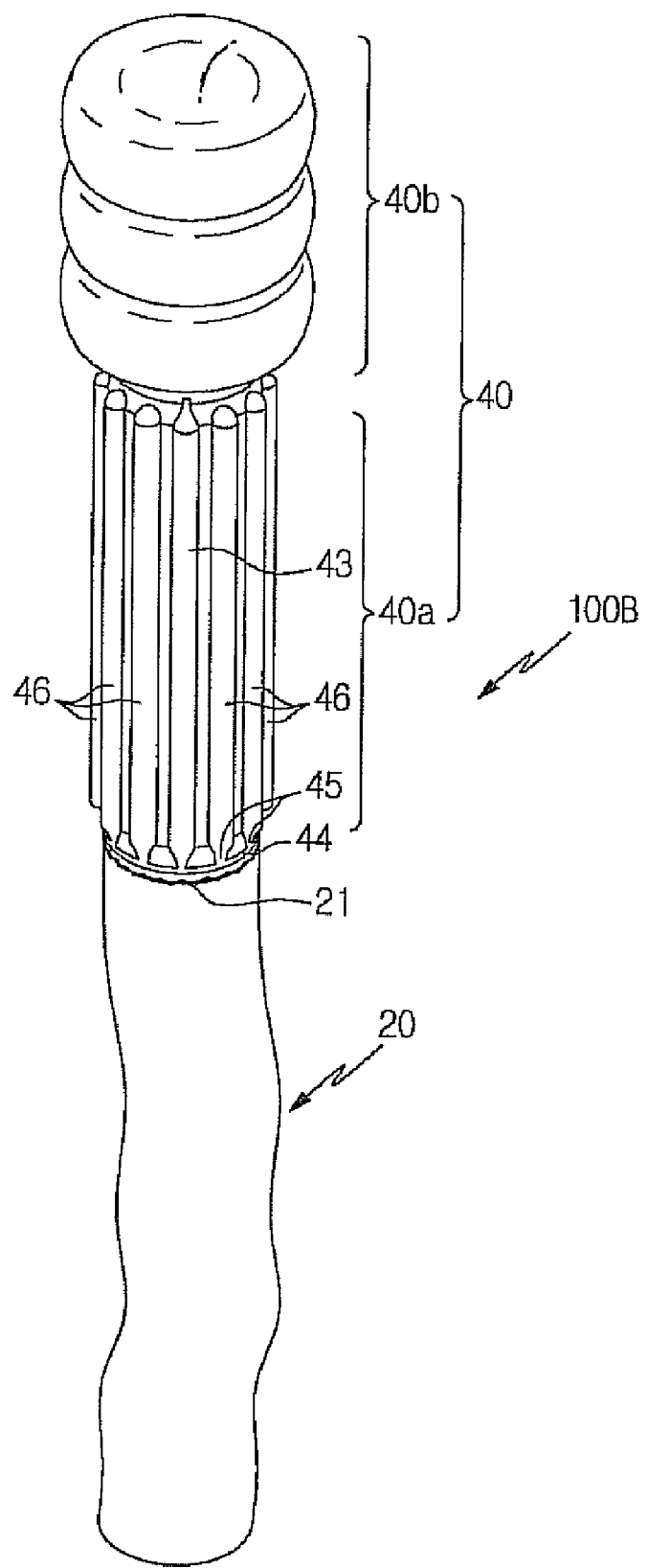
FIG. 4A is a perspective view illustrating a balloon type stent system for treatment of obesity according to another embodiment of the present invention.
Figure 4B:
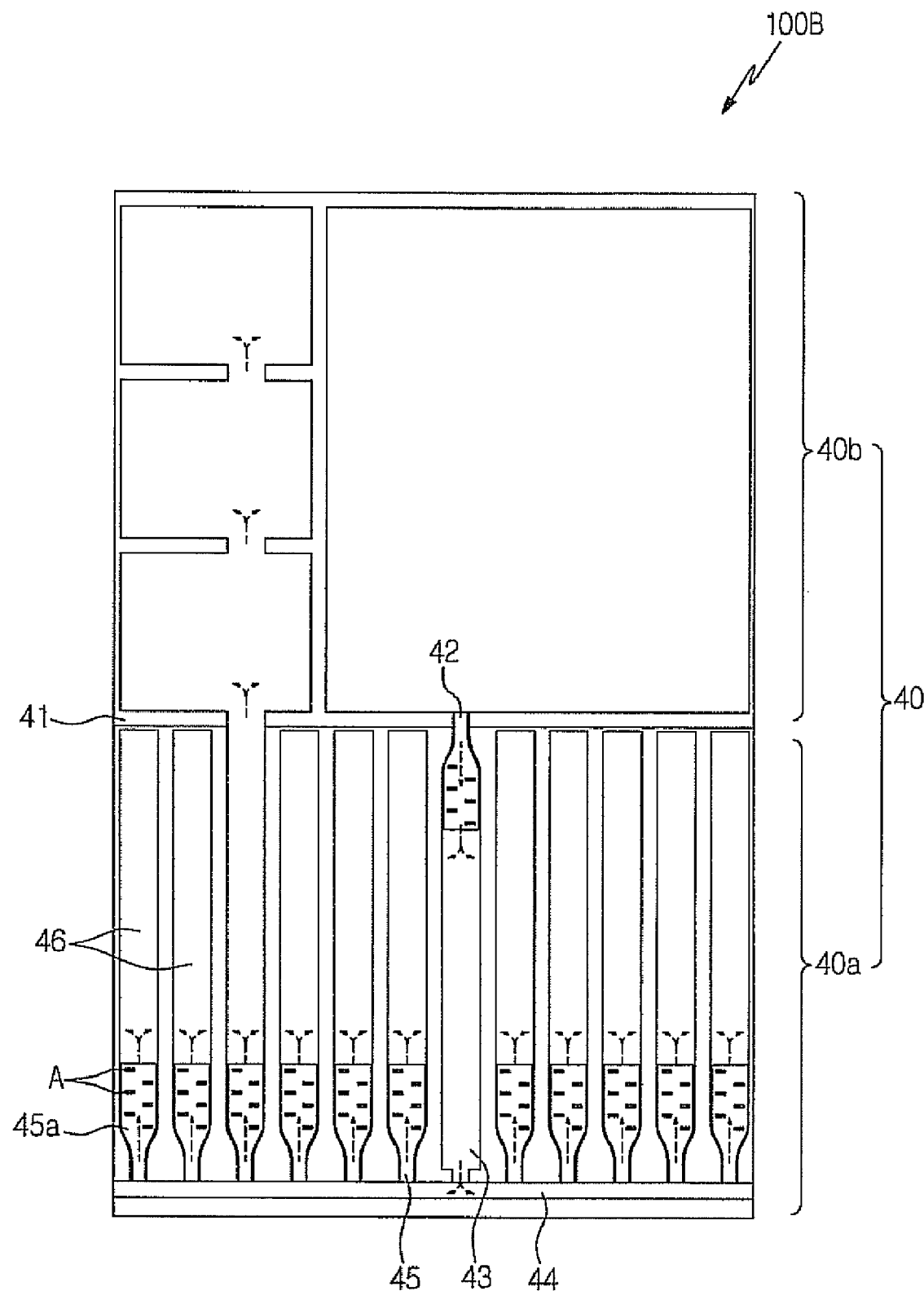
FIG. 4B is a development view of FIG. 4A.

As shown in FIGS. 4A and 4B, a plurality of doughnut type expansion units 40b may be provided in a state in which the doughnut type expansion units 40b communicate with one another. The doughnut type expansion units 40b may be located in a body 203 of the stomach 200 such that an obese patient feels full.

Figure 5A:
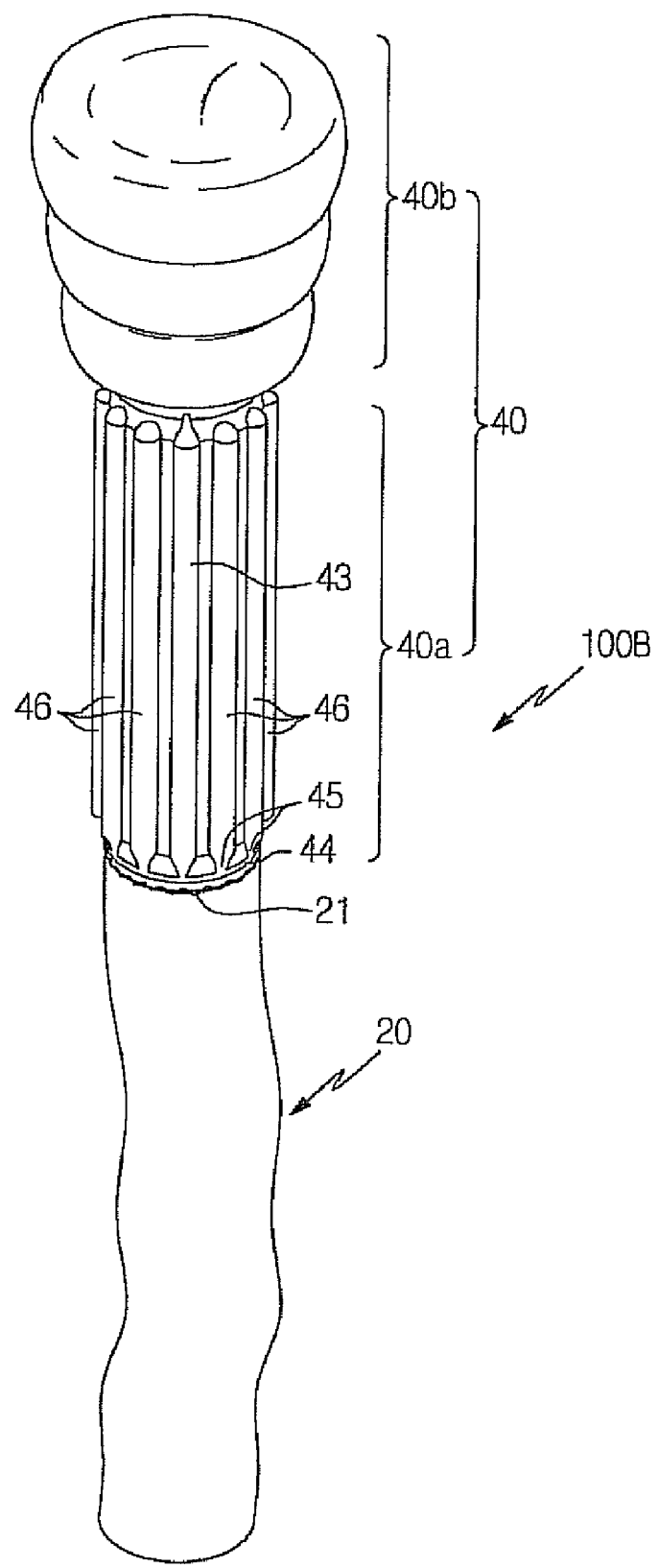
FIG. 5A is a perspective view illustrating a balloon type stent system for treatment of obesity according to another embodiment of the present invention.
Figure 5B:
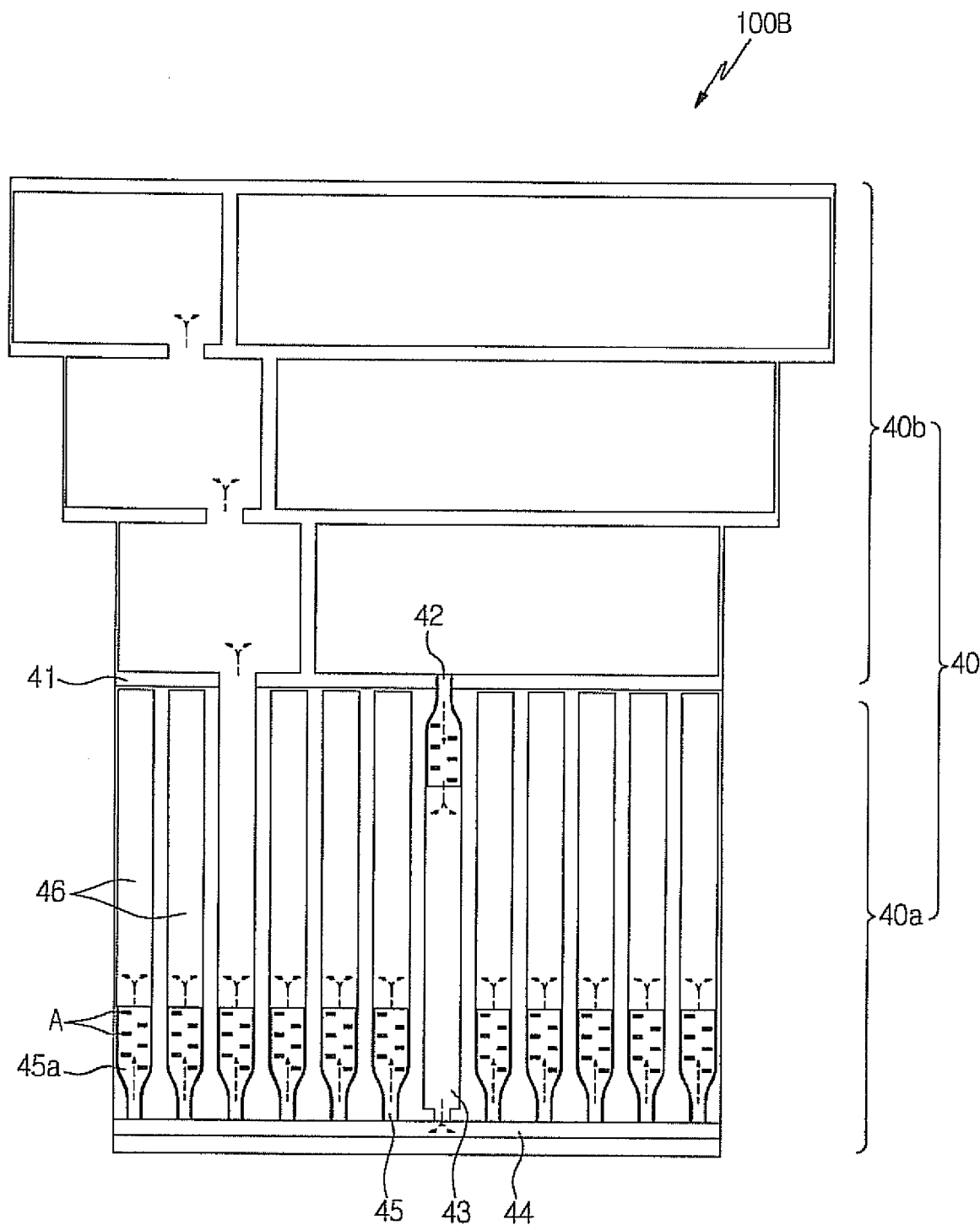
FIG. 5B is a development view of FIG. 3A.
Figure 6:
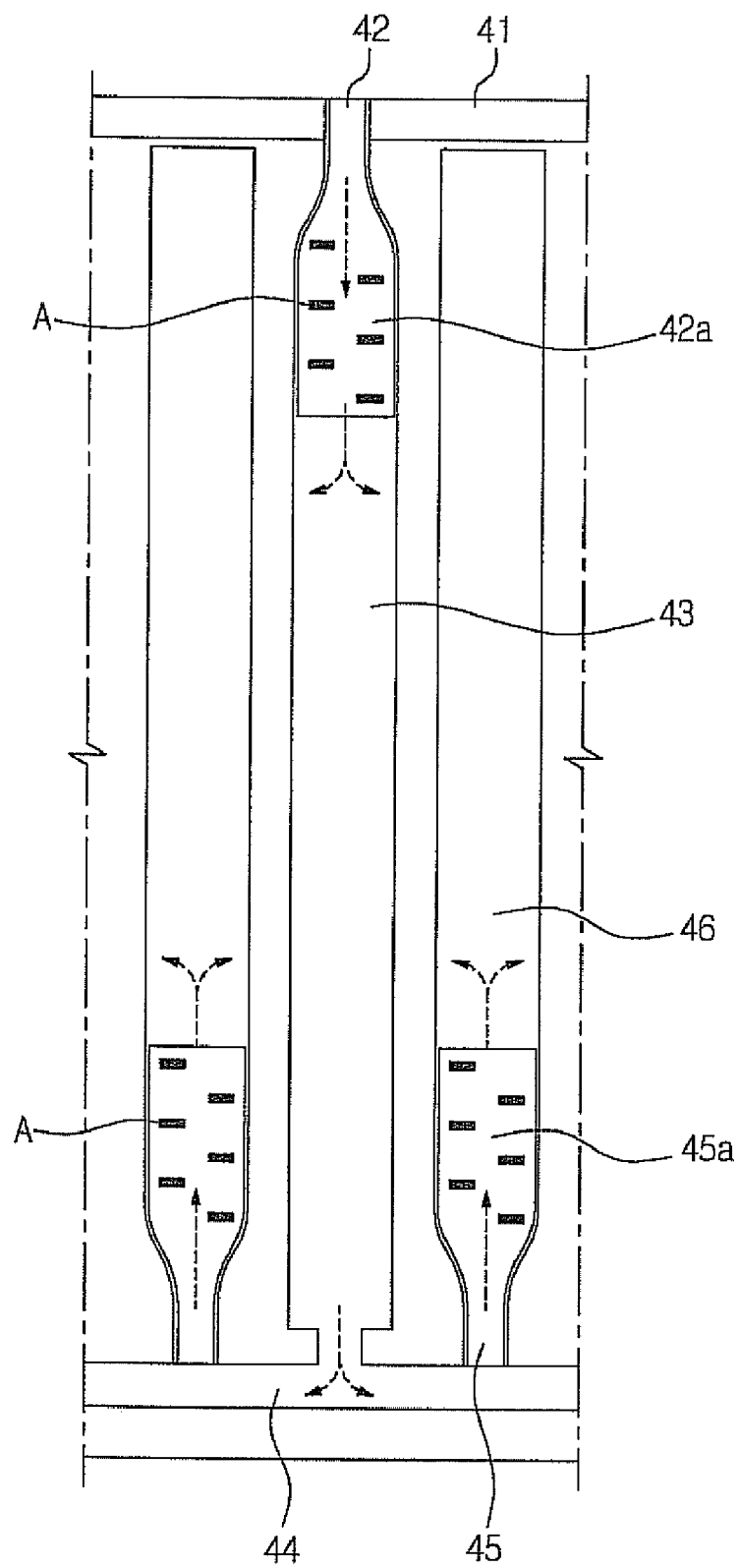
FIG. 6 is a partially front development view illustrating a balloon type stent unit.
Figure 7A:
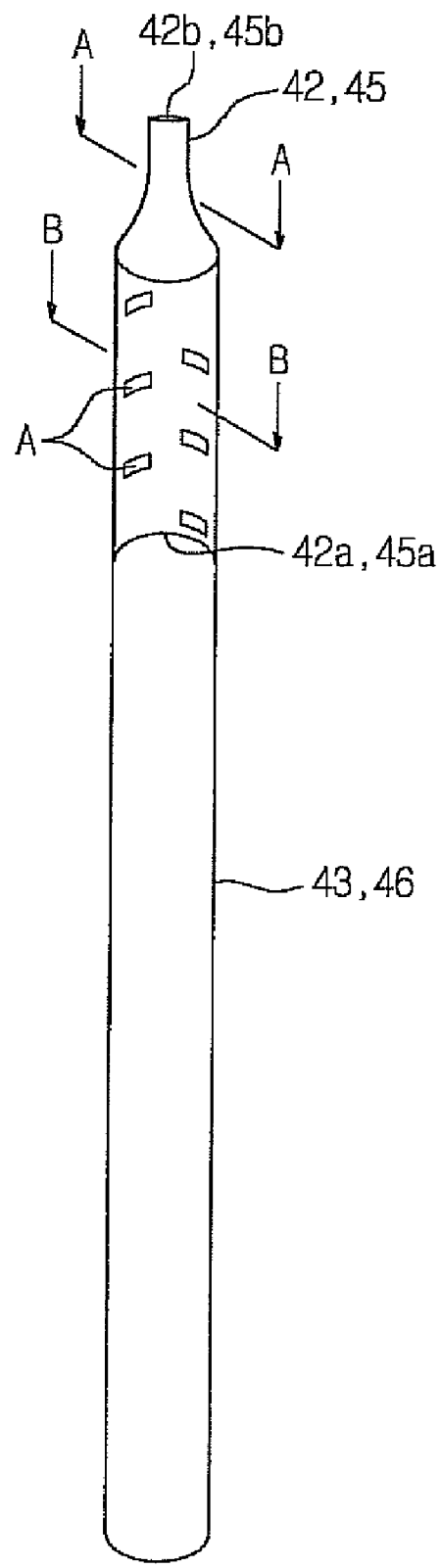
FIG. 7A is a perspective view illustrating an injection expansion unit or a distribution expansion unit.
Figure 7B:
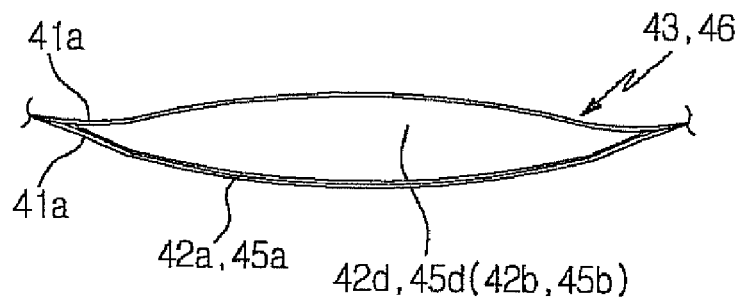
FIG. 7B is a sectional view taken along line A-A of FIG. 7A before the injection expansion unit or the distribution expansion unit is filled with an expansion agent.
Figure 7C:
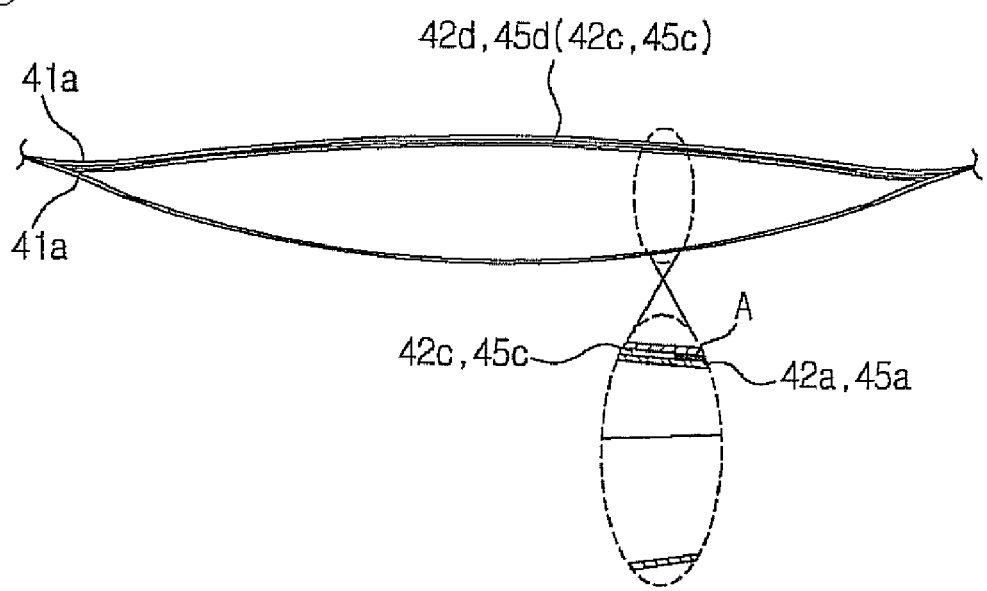
FIG. 7C is a sectional view taken along line B-B of FIG. 7A before the injection expansion unit or the distribution expansion unit is filled with an expansion agent.
Figure 7D:
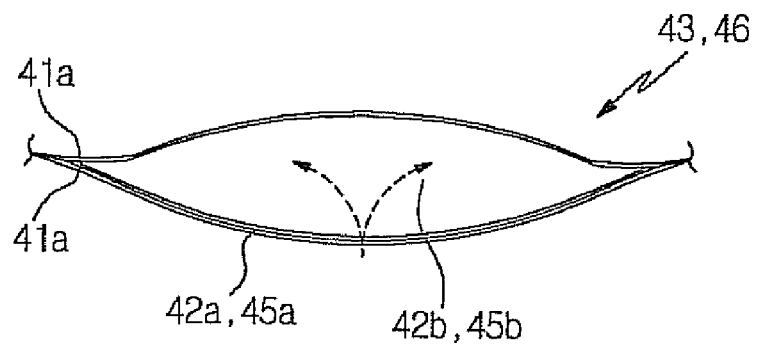
FIG. 7D is a sectional view taken along line A-A of FIG. 7A after the injection expansion unit or the distribution expansion unit is filled with an expansion agent.
Figure 7E:
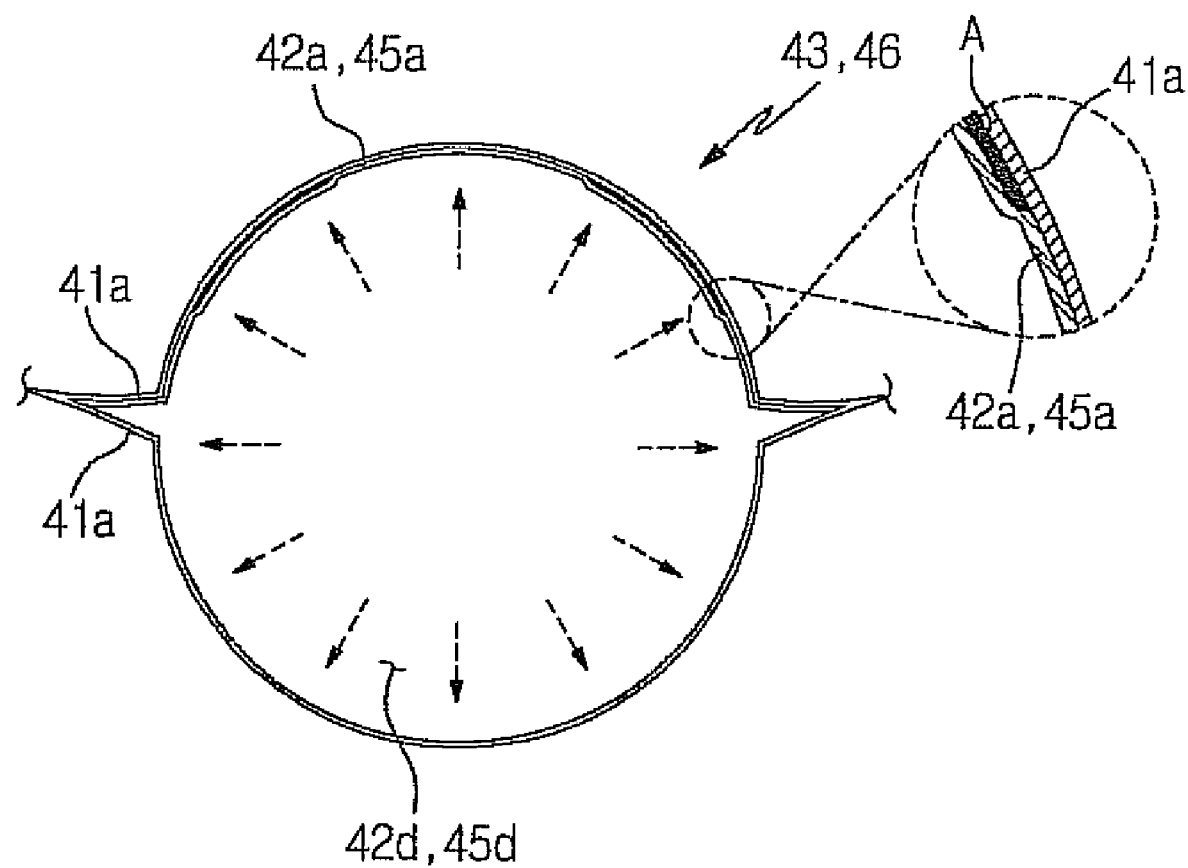
FIG. 7E is a sectional view taken along line B-B of FIG. 7A after the injection expansion unit or the distribution expansion unit is filled with an expansion agent.
Figure 7F:
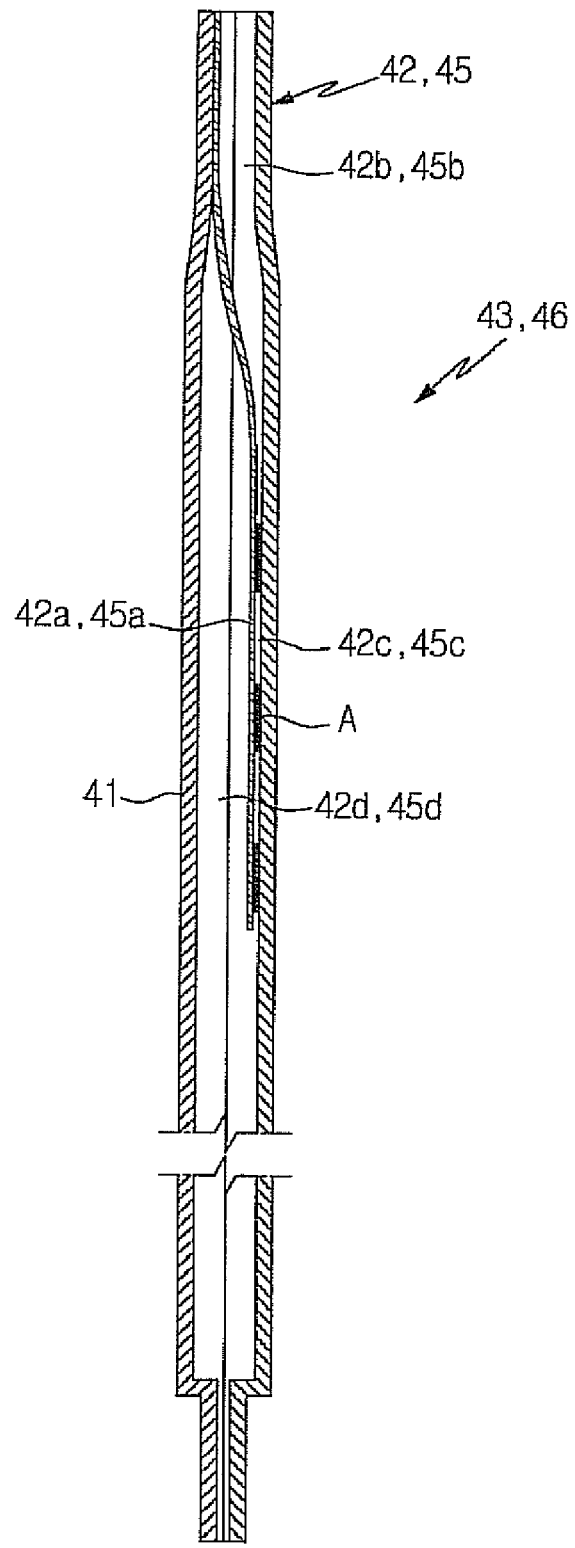
FIG. 7F is a sectional view illustrating a state in which the injection expansion unit or the distribution expansion unit is not filled with an expansion agent.
Figure 7G:
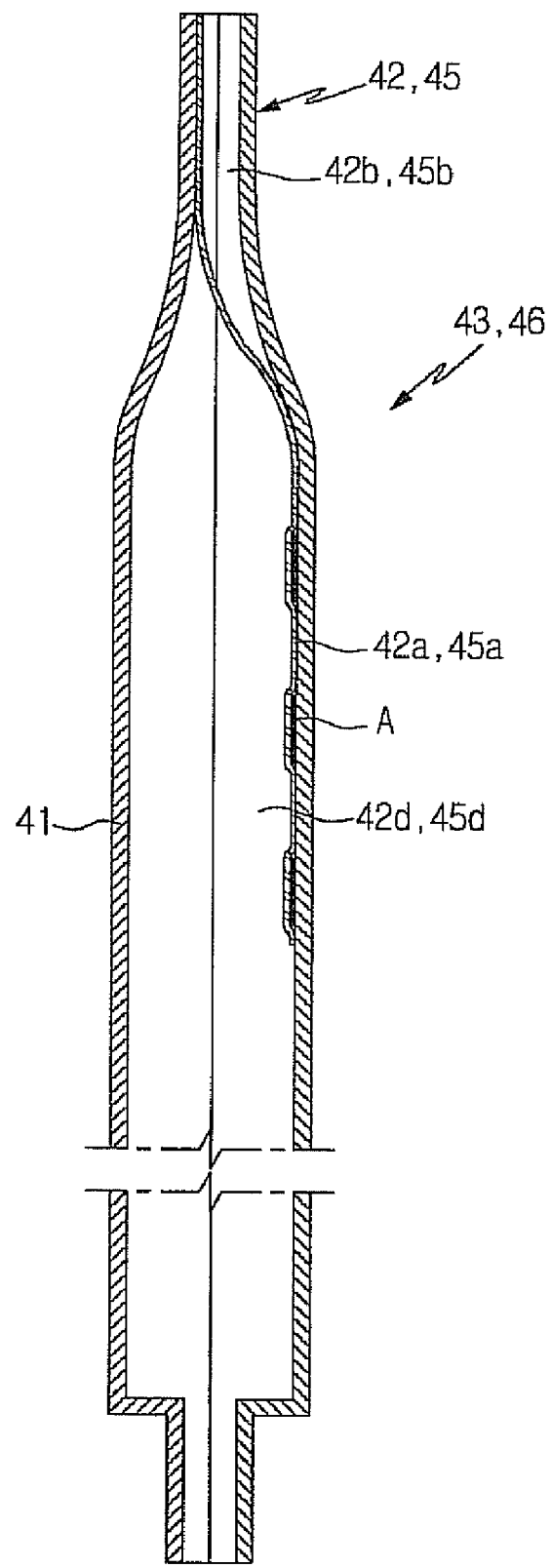
FIG. 7G is a sectional view illustrating a state in which the injection expansion unit or the distribution expansion unit is filled with an expansion agent and an expansion agent discharge prevention film is pressed to prevent discharge of the expansion agent.
Figure 8:
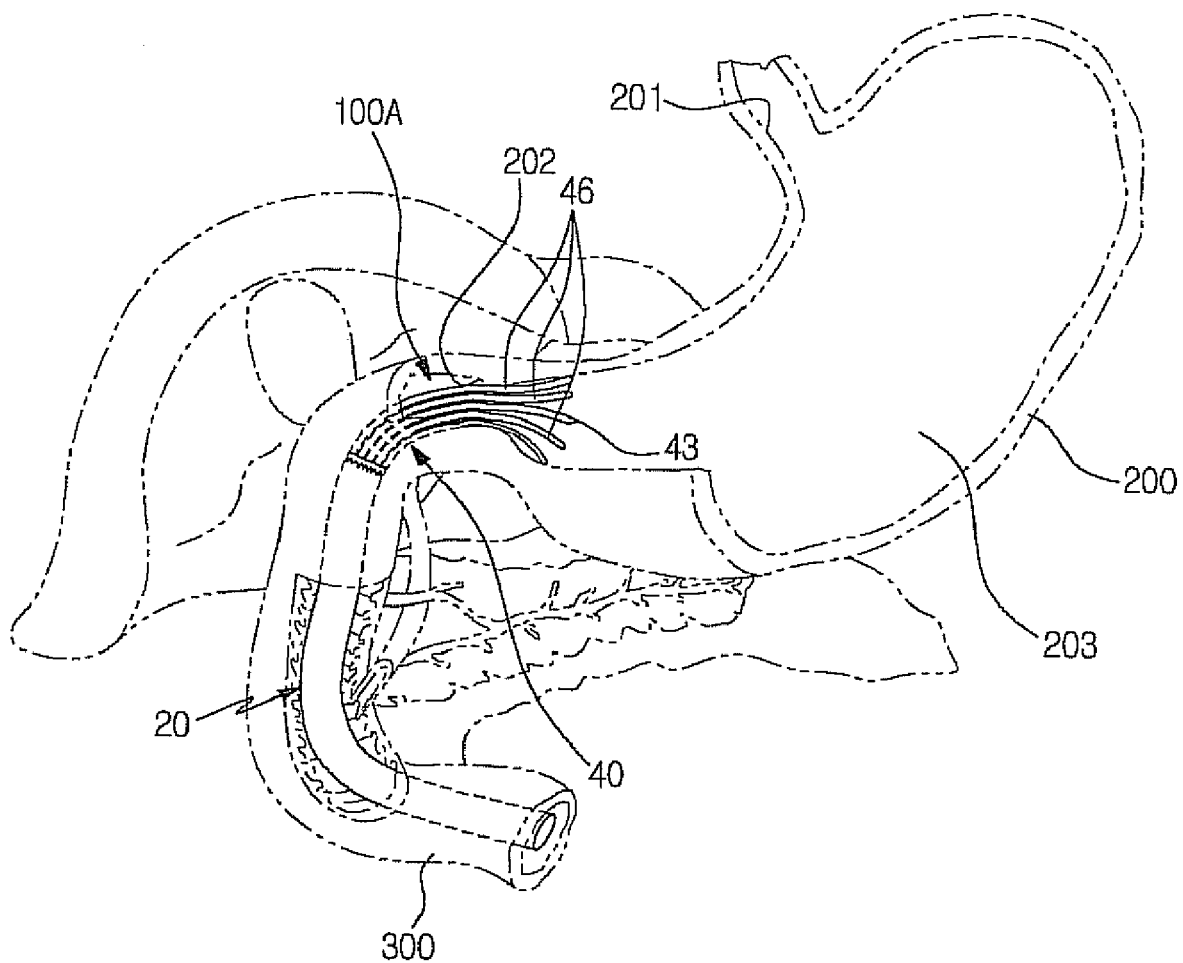
FIG. 8 is a view illustrating a surgical operation using the balloon type stent system for treatment of obesity of FIG. 1.
Figure 9:
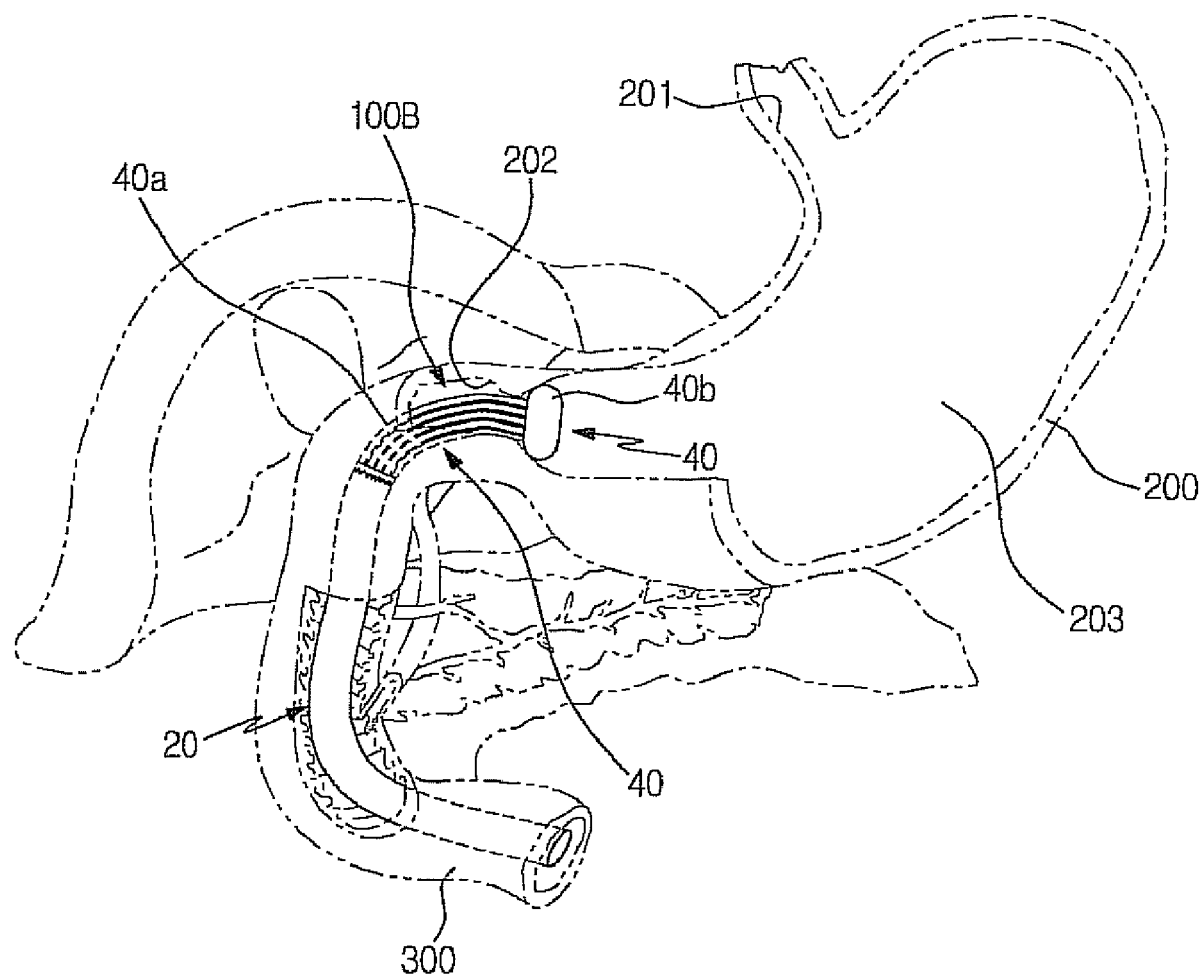
FIG. 9 is a view illustrating a surgical operation using the balloon type stent system for treatment of obesity of FIG. 3A.

As shown in FIGS. 5A and 5B, the doughnut type expansion units 40b may have gradually increased diameters. That is, the diameters of the doughnut type expansion units 40b may be gradually increased from the doughnut type expansion unit 40b connected to the cylindrical expansion unit 40a to the outermost doughnut type expansion unit 40b remote from the cylindrical expansion unit 40a such that food digested in the stomach 200 can be easily discharged through the doughnut type expansion units 40b.

As shown in FIGS. 3A, 3B, and 6 to 7G, the tube 20 is formed in the shape of a cylinder which is flexible and thin. The tube 20 has a length corresponding to the length of the lumen of the duodenum 300. The tube 20 is connected to the lower end of the stent unit body 41 at the cylindrical expansion unit 40a of the balloon type stent unit 40. The tube 20 is connected to the stent unit body 41 by a connection wire 21.

The injection expansion unit 43 and the distribution expansion units 46 of the balloon type stent unit 40 have expansion spaces 42d and 45d communicating with the expansion injection port 42 and the distribution injection ports 45, respectively. The injection expansion unit 43 and the distribution expansion units 46 of the balloon type stent unit 40 are formed in the shape of a bottle.

Also, ends of expansion agent discharge prevention films 42a and 45a, formed in the shape of a bottle, at which each of the expansion agent discharge prevention films 42a and 45a has a small area are attached to inner walls of the expansion injection port 42 and the distribution injection ports 45 so as to form injection spaces 42b and 45b.

On the other hand, ends of the expansion agent discharge prevention films 42a and 45a at which each of the expansion agent discharge prevention films 42a and 45a has a large area are locally attached, through thermal binding A, to inner walls of the expansion spaces 42d and 45d opposite to the sides at which the small area ends of the expansion agent discharge prevention films 42a and 45a are attached so as to form filling spaces 42c and 45c.

That is, when the expansion agent is injected through the injection spaces 42b and 45b, the filling spaces 42c and 45c are filled with the expansion agent. As a result, the expansion agent discharge prevention films 42a and 45a are pressed by the expansion agent. Consequently, the injection spaces 42b and 45b are closed, and the expansion agent discharge prevention films 42a and 45a come into tight contact with the inner walls of the expansion spaces 42d and 45d to prevent discharge of the expansion agent.

Hereinafter, the operation of the balloon type stent system for treatment of obesity according to the present invention with the above-stated construction will be described in detail with the accompanying drawings.

As shown in FIGS. 1, 2, 6 to 7G, and 8, the obesity prevention system 100A is manufactured by connecting the tube 20 to the lower end of the balloon type stent unit 40 using the connection wire 21. The volume of the balloon type stent unit 40 is reduced, and then the expansion agent injection port 42 of the balloon type stent unit 40 is connected to the end of an additional catheter (not shown) for a surgical operation such that the expansion agent does not leak.

Subsequently, the catheter is inserted into the body 203 of the stomach 200 through the cardia 201 of the stomach 200, and then the tube 20 and the integrated expansion unit 47 are inserted into the pylorus 202 of the stomach 200, using raparoscopic surgery.

At this time, the tube 20 extends through the lumen of the duodenum 300, and the integrated expansion unit 47 is inserted into the lumen at which the pylorus 202 of the stomach 200 is connected to the duodenum 300.

In addition, the separated expansion unit 48 is disposed adjacent to the inner wall of the body 203 of the stomach 200 at which the pylorus 202 of the stomach 200 is located.

Subsequently, an expansion agent is injected into the balloon type stent unit 40 through the expansion agent injection port 42 using the catheter.

Upon injection of the expansion agent as described above, the expansion agent is distributed into the distribution expansion units 46 through the injection expansion unit 43 and the distribution channel 44. As a result, the stent unit body 41 expands into the shape of a cylindrical tube, and therefore, the injection expansion unit 43 and the distribution expansion units 46 constituting the integrated expansion unit 47 expand to push the inner wall of the lumen at which the pylorus 202 of the stomach 200 is connected to the duodenum 300 in all directions such that the inner wall of the lumen is supported.

At the same time, the injection expansion unit 43 and the distribution expansion units 46 constituting the separated expansion unit 48 expand. As a result, the injection expansion unit 43 and the distribution expansion units 46 constituting the separated expansion unit 48 are bent outward to come into tight contact with the inner wall of the body 203 of the stomach 200.

That is, the injection expansion unit 43 and the distribution expansion units 46 constituting the separated expansion unit 48 are caught by the inner wall of the body 203 of the stomach 200 connected to the pylorus 202 of the stomach 200 to prevent the obesity prevention stent system 100A from being dislocated due to food moving to the duodenum 300.

At this time, the expansion agent is introduced through the injection space 42b such that the filling space 42c is filled with the expansion agent. As a result, the remainder of the expansion agent moves through the distribution channel 44 and is then introduced through the injection spaces 45b of some of the distribution expansion units 46 adjacent to the injection expansion unit 43 such that the filling spaces 45c are filled with the expansion agent. The same process is repeatedly carried out such that the remaining distribution expansion units 46 are filled with the expansion agent.

More specifically, when the expansion agent is injected through the injection spaces 42b and 45b, the filling spaces 42c and 45c, formed by local tight contact between the expansion agent discharge prevention films 42a and 45a and the inner walls of the expansion spaces 42d and 45d, are filled with the expansion agent. When the filling of the filling spaces 42c and 45c with the expansion agent is completed, the expansion agent discharge prevention films 42a and 45a are pressed in all directions to close the injection spaces 42b and 45b. In addition, the expansion agent discharge prevention films 42a and 45a come into tight contact with the inner walls of the filling spaces 42c and 45c to prevent discharge of the expansion agent.

When the spaces of the injection expansion unit 43 and the distribution expansion units 46 are fully filled with the expansion agent, with the result that the spaces of the injection expansion unit 43 and the distribution expansion units 46 are not filled with the expansion agent any more, the connection between the catheter and the expansion agent injection port 42 is broken, and therefore, the catheter is separated from the balloon type stent unit 40.

That is, resistance pressure of the connection between the catheter and the expansion agent injection port 42 is formed to be less than resistance pressure of the synthetic vinyl 41a of the balloon type stent unit 40. Consequently, the connection between the catheter and the expansion agent injection port 42 is broken, and therefore, the catheter is separated from the balloon type stent unit 40.

During injection of the expansion agent, the lower parts of the expansion agent discharge prevention films 42a and 45a come into tight contact with the opposite inner walls of the injection expansion unit 43 and the distribution expansion units 46 at the opposite sides thereof, while the upper parts of the expansion agent discharge prevention films 42a and 45a are not dislocated, thereby preventing discharge of the expansion agent.

When an obese patient takes food after the obesity prevention stent system 100A is inserted into a body of the obese patient through a surgical operation, the food moves along the gullet of the obese patient and is minutely decomposed in the body 203 of the stomach 200 of the obese patient. Subsequently, the minutely decomposed food passes through the integrated expansion unit 47 of the balloon type stent unit 40 and directly moves into the small intestine along the tube 20 such that the minutely decomposed food is digested and absorbed by the small intestine.

That is, the food, having passed through the balloon type stent unit 40, passes through the duodenum 300 along the tube 20 without digestion and absorption and then moves into the small intestine. As a result, some nutritive substances of the food are absorbed by the small intestine, and the remaining nutritive substances of the food moves into the large intestine.

Consequently, nutrition absorptivity in the duodenum 300 is reduced, and therefore, a degree of obesity of the obese patient is lowered.

In this way, the food directly moves into the small intestine through the balloon type stent unit 40 and the tube 20 such that nutritive substances of the food are digested and absorbed by the small intestine, thereby reducing nutrition absorptivity in the duodenum 300 and thus lowering a degree of obesity of the obese patient.

As shown in FIGS. 3A, 3B, 6 to 7G, and 8, the obesity prevention system 100B is manufactured by connecting the tube 20 to the lower end of the balloon type stent unit 40 using the connection wire 21.

Next, the volume of the balloon type stent unit 40 is reduced, and then the expansion agent injection port 42 of the balloon type stent unit 40 is connected to the end of an additional catheter (not shown) for a surgical operation such that the expansion agent does not leak.

Subsequently, the catheter is inserted into the body 203 of the stomach 200 through the cardia 201 of the stomach 200, and then the tube 20 and the cylindrical expansion unit 40a are inserted into the pylorus 202 of the stomach 200, using raparoscopic surgery.

At this time, the tube 20 extends through the lumen of the duodenum 300, and the cylindrical expansion unit 40a is inserted into the lumen at which the pylorus 202 of the stomach 200 is connected to the duodenum 300.

In addition, the doughnut type expansion unit 40b is disposed adjacent to the inner wall of the body 203 of the stomach 200 at which the pylorus 202 of the stomach 200 is located.

Subsequently, an expansion agent is injected into the balloon type stent unit 40 through the expansion agent injection port 42 using the catheter.

Upon injection of the expansion agent as described above, the expansion agent is distributed into the distribution expansion units 46 through the injection expansion unit 43 and the distribution channel 44. As a result, the injection expansion unit 43 and the distribution expansion units 46 constituting the cylindrical expansion unit 40a expand to push the inner wall of the lumen at which the pylorus 202 of the stomach 200 is connected to the duodenum 300 in all directions such that the inner wall of the lumen is supported.

At the same time, the doughnut type expansion unit 40b expands to come into tight contact with the inner wall of the body 203 of the stomach 200.

At this time, the doughnut type expansion unit 40b is caught by the inner wall of the body 203 of the stomach 200 connected to the pylorus 202 of the stomach 200 to prevent the obesity prevention stent system 100B from being dislocated due to food moving to the duodenum 300.

More specifically, the expansion agent is introduced through the injection space 42b of the cylindrical expansion unit 40a such that the filling space 42c is filled with the expansion agent. As a result, the remainder of the expansion agent moves through the distribution channel 44 and is then introduced through the injection spaces 45b of some of the distribution expansion units 46 adjacent to the injection expansion unit 43 such that the filling spaces 45c are filled with the expansion agent. The same process is repeatedly carried out such that the remaining distribution expansion units 46 are filled with the expansion agent.

At this time, when one of the distribution expansion units 46, which communicate with the doughnut type expansion unit 40b, is filled with the expansion agent, the expansion agent moves to the doughnut type expansion unit 40b, which is filled with the expansion agent, and then the expansion agent flows to the remaining distribution expansion units 46 to expand the remaining distribution expansion units 46.

That is, when the expansion agent is injected through the injection spaces 42b and 45b, the filling spaces 42c and 45c are filled with the expansion agent through the filling spaces 42c and 45c, formed by local tight contact between the expansion agent discharge prevention films 42a and 45a and the inner walls of the expansion spaces 42d and 45d, are filled with the expansion agent. When the filling of the filling spaces 42c and 45c with the expansion agent is completed, the expansion agent discharge prevention films 42a and 45a are pressed in all directions to close the injection spaces 42b and 45b. In addition, the expansion agent discharge prevention films 42a and 45a come into tight contact with the inner walls of the filling spaces 42c and 45c to prevent discharge of the expansion agent.

When the spaces of the injection expansion unit 43 and the distribution expansion units 46 are fully filled with the expansion agent, with the result that the spaces of the injection expansion unit 43 and the distribution expansion units 46 are not filled with the expansion agent any more, the connection between the catheter and the expansion agent injection port 42 is broken, and therefore, the catheter is separated from the balloon type stent unit 40.

That is, resistance pressure of the connection between the catheter and the expansion agent injection port 42 is formed to be less than resistance pressure of the synthetic vinyl 41a of the balloon type stent unit 40. Consequently, the connection between the catheter and the expansion agent injection port 42 is broken, and therefore, the catheter is separated from the balloon type stent unit 40.

During injection of the expansion agent, the lower parts of the expansion agent discharge prevention films 42a and 45a come into tight contact with the opposite inner walls of the injection expansion unit 43 and the distribution expansion units 46 at the opposite sides thereof, while the upper parts of the expansion agent discharge prevention films 42a and 45a are not dislocated, thereby preventing discharge of the expansion agent.

When an obese patient takes food after the obesity prevention stent system 100B is inserted into a body of the obese patient through a surgical operation, the food moves along the gullet of the obese patient and is minutely decomposed in the body 203 of the stomach 200 of the obese patient. Subsequently, the minutely decomposed food passes through the cylindrical expansion unit 40a of the balloon type stent unit 40 and directly moves into the small intestine along the tube 20 such that the minutely decomposed food is digested and absorbed by the small intestine.

That is, the food, having passed through the balloon type stent unit 40, passes through the duodenum 300 along the tube 20 without digestion and absorption and then moves into the small intestine. As a result, some nutritive substances of the food are absorbed by the small intestine, and the remaining nutritive substances of the food move into the large intestine.

Consequently, nutrition absorptivity in the duodenum 300 is reduced, and therefore, a degree of obesity of the obese patient is lowered.

In this way, the food directly moves into the small intestine through the balloon type stent unit 40 and the tube 20 such that nutritive substances of the food are digested and absorbed by the small intestine, thereby reducing nutrition absorptivity in the duodenum 300 and thus lowering a degree of obesity of the obese patient.

Figure 10:
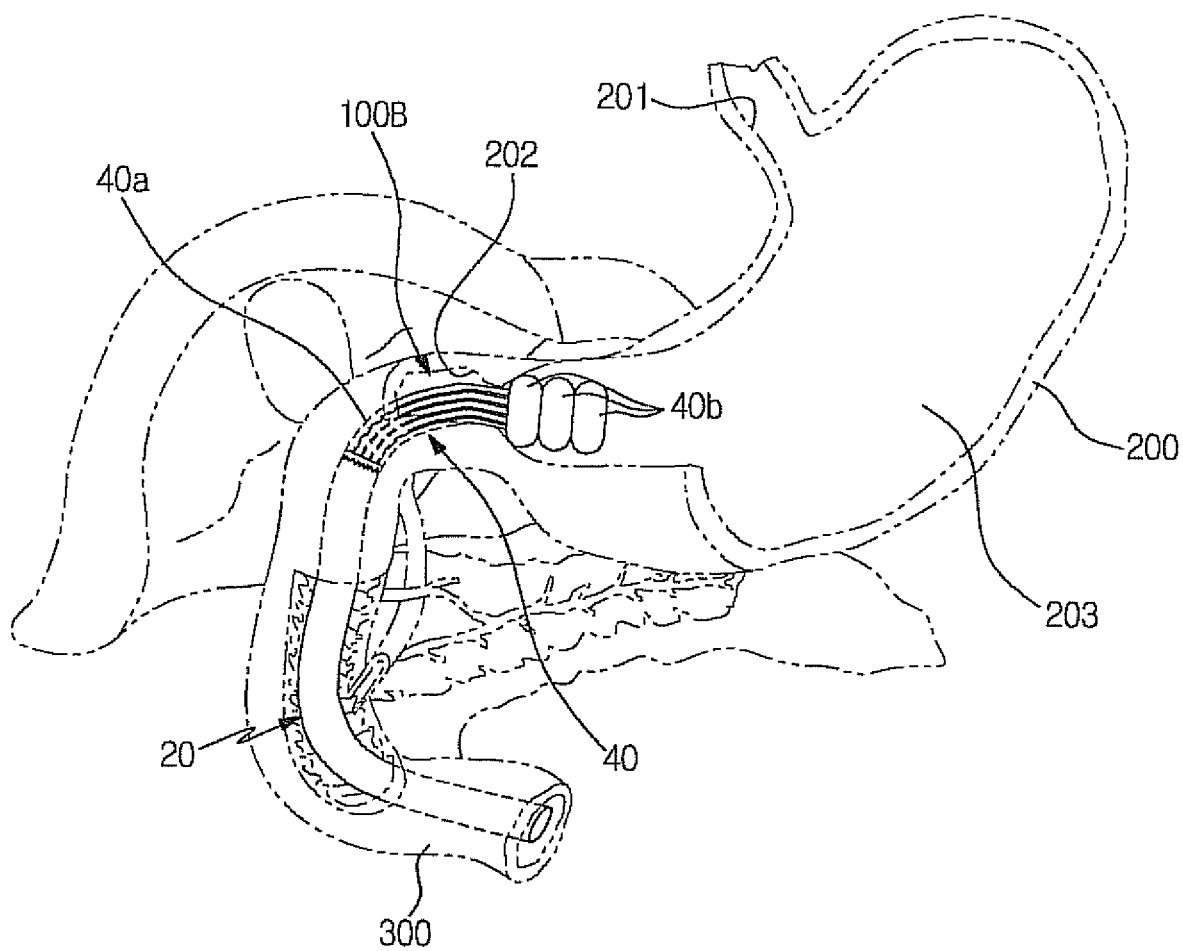
FIG. 10 is a view illustrating a surgical operation using the balloon type stent system for treatment of obesity of FIG. 4A.

In the balloon type stent unit 40 including a plurality of doughnut type expansion units 40b, as shown in FIGS. 4A, 4B, and 10, a plurality of doughnut type expansion units 40b expand to reduce the volume of the internal space of the body 203 of the stomach 200 such that the obese patient feels full.

Figure 11:
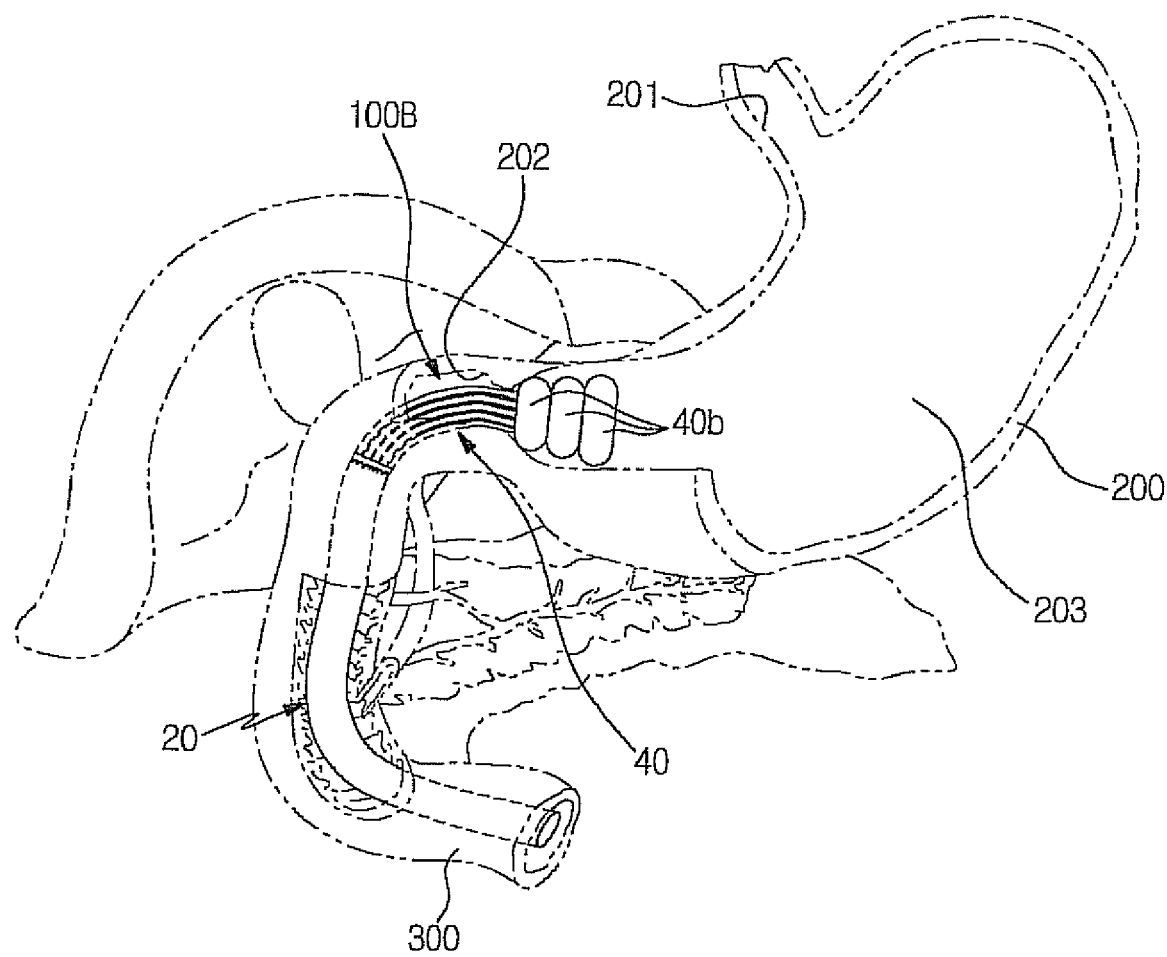
FIG. 11 is a view illustrating a surgical operation using the balloon type stent system for treatment of obesity of FIG. 5A.

In the balloon type stent unit 40 including a plurality of doughnut type expansion units 40b having gradually increased diameters, as shown in FIGS. 5A, 5B, and 11, the doughnut type expansion units 40b come into tight contact with the inner wall of the body 203 of the stomach 200 upon expansion of the doughnut type expansion units 40b, thereby preventing dislocation of the balloon type stent unit 40 due to movement of the food in addition to enabling the obese patient to feel full.

In conclusion, food directly moves into the small intestine along the balloon type stent unit 40 and the tube 20 such that the food is digested and absorbed by the small intestine, thereby reducing nutrition absorptivity in the duodenum 300 and thus lowering a degree of obesity of the obese patient.

In addition, although one of the distribution expansion units 46 is broken to cause leakage of the expansion agent, the remaining distribution expansion units 46 keep expanding, thereby achieving smooth movement of the food.

As is apparent from the above description, the balloon type stent system for treatment of obesity according to the present invention is characterized in that food digested in the stomach moves through the duodenum along the tube of the balloon type stent system for treatment of obesity, such that the food is prevented from being converted into nutritive substances through enzymatic decomposition caused by bile in the duodenum and thus the nutritive substances is prevented from being absorbed by the duodenum. Consequently, the present invention has the effect of lowering a degree of obesity of an obese patient having the balloon type stent system for treatment of obesity according to the present invention inserted therein through a surgical operation and thus effectively treating obesity of the obese patient.

Also, the balloon type stent system for treatment of obesity according to the present invention is characterized in that the doughnut type expansion unit is inserted into the body of the stomach. Consequently, the present invention has the effect of enabling the obese patient to feel full.

In addition, the balloon type stent system for treatment of obesity according to the present invention is characterized in that a plurality of doughnut type expansion units are provided, and one of the doughnut type expansion units positioned at the center of the body of the stomach has the largest diameter. Consequently, the present invention has the effect of achieving smooth movement of the food decomposed in the stomach.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A balloon type stent system for treatment of obesity configured such that an injection expansion unit and a plurality of distribution expansion units extend in a longitudinal direction of a stent unit body formed by coupling two sheets of synthetic vinyl in the shape of a cylinder, the injection expansion unit and a plurality of distribution expansion units are divided uniformly along a circumference of the stent unit body, the injection expansion unit has an expansion agent injection port formed at one end thereof, and the distribution expansion units each have a distribution injection port communicating with a distribution channel formed in a circumferential direction of the stent unit body such that the distribution channel communicates with the other end of the injection expansion unit opposite to the end of the injection expansion unit at which the expansion agent injection port is formed in a longitudinal direction of the injection expansion unit, such that connection ends interconnecting the injection expansion unit and the distribution expansion units formed at the stent unit body are partially cut in a longitudinal direction such that the expansion units are divided into an integrated expansion unit and a separated expansion unit, the injection expansion unit and the distribution expansion units constituting the separated expansion unit are bent outward to form a balloon type stent unit, and such that a tube is formed in the shape of a cylinder which is flexible and thin, the tube is configured to have a length corresponding to a length of a lumen of a duodenum of an obese patient having the balloon type stent system for treatment of obesity inserted therein, and the tube is connected to a lower end of the stent unit body at a side where the integrated expansion unit of the balloon type stent unit is formed by a connection wire, wherein the integrated expansion unit configured to expand in the shape of a cylindrical tube by an expansion agent sequentially distributed to the injection expansion unit, the distribution channel, and the distribution expansion units constituting the integrated expansion unit and the separated expansion unit when the expansion agent is injected into the balloon type stent unit through the expansion agent injection port using a catheter provided to inject the expansion agent is configured to be inserted into a pylorus of a stomach, which is an outlet of the stomach, the tube is configured to be inserted into the lumen of the duodenum, and the separated expansion unit is configured to be caught by internal walls of the pylorus and the body of the stomach such that food directly moves into a small intestine, where the food is digested and absorbed, through the balloon type stent unit and the tube, thereby reducing nutrition absorptivity in the duodenum and thus lowering a degree of obesity of the obese patient.

2. The balloon type stent system for treatment of obesity according to claim 1, wherein the injection expansion unit and the distribution expansion units of the balloon type stent unit have expansion spaces communicating with the expansion injection port and the distribution injection ports, respectively, the injection expansion unit and the distribution expansion units of the balloon type stent unit are formed in the shape of a bottle, ends of expansion agent discharge prevention films are formed in the shape of a bottle, at which each of the expansion agent discharge prevention films has a small area attached to inner walls of the expansion injection port and the distribution injection ports so as to form injection spaces; ends of the expansion agent discharge prevention films at which each of the expansion agent discharge prevention films has a large area are locally attached through thermal binding to inner walls of the expansion spaces opposite to the sides at which the small area ends of the expansion agent discharge prevention films are attached so as to form filling spaces, whereby, when the expansion agent is injected through the injection spaces, the filling spaces are filled with the expansion agent, with the result that the expansion agent discharge prevention films are pressed by the expansion agent, thereby closing the injection spaces such that the expansion agent discharge prevention films come into tight contact with the inner walls of the expansion spaces to prevent discharge of the expansion agent.

3. A balloon type stent system for treatment of obesity configured such that an injection expansion unit and a plurality of distribution expansion units extend in a longitudinal direction of a stent unit body formed by coupling two sheets of synthetic vinyl in the shape of a cylinder, the injection expansion unit and the distribution expansion units are divided uniformly along a circumference of the stent unit body, the injection expansion unit has an expansion agent injection port formed at one end thereof, the distribution expansion units each have a distribution injection port communicating with a distribution channel formed in a circumferential direction of the stent unit body such that the distribution channel communicates with the other end of the injection expansion unit opposite to the end of the injection expansion unit at which the expansion agent injection port is formed in a longitudinal direction of the injection expansion unit, and the injection expansion unit and the distribution expansion units constitute a cylindrical expansion unit, such that a doughnut type expansion unit is connected to the stent unit body of the cylindrical expansion unit such that the doughnut type expansion unit communicates with one of the distribution expansion units, the doughnut type expansion unit is configured to expand in the shape of a doughnut upon expansion of the doughnut type expansion unit, and the cylindrical expansion unit and the doughnut type expansion unit constitute a balloon type stent unit, and such that a tube is formed in the shape of a cylinder which is flexible and thin, the tube configured to have a length corresponding to a length of a lumen of a duodenum of an obese patient having the balloon type stent system for treatment of obesity inserted therein, and the tube is connected to a lower end of the stent unit body of the cylindrical expansion unit by a connection wire, wherein the cylindrical expansion unit configured to expand in the shape of a cylindrical tube by an expansion agent distributed to the injection expansion unit, the distribution channel, and the distribution expansion units, and, at the same time, to the doughnut type expansion unit when the expansion agent is injected into the balloon type stent unit through the expansion agent injection port using a catheter provided to inject the expansion agent is configured to be inserted into a pylorus of a stomach, which is an outlet of the stomach, the tube is configured to be inserted into the lumen of the duodenum, and the doughnut type expansion unit is configured to be caught by internal walls of the pylorus and the body of the stomach such that food directly moves into a small intestine, where the food is digested and absorbed, through the balloon type stent unit and the tube, thereby reducing nutrition absorptivity in the duodenum and thus lowering a degree of obesity of the obese patient.

4. The balloon type stent system for treatment of obesity according to claim 3, wherein the injection expansion unit and the distribution expansion units of the balloon type stent unit have expansion spaces communicating with the expansion injection port and the distribution injection ports, respectively; the injection expansion unit and the distribution expansion units of the balloon type stent unit are formed in the shape of a bottle, ends of expansion agent discharge prevention films are formed in the shape of a bottle, at which each of the expansion agent discharge prevention films has a small area is attached to inner walls of the expansion injection port and the distribution injection ports so as to form injection spaces, ends of the expansion agent discharge prevention films at which each of the expansion agent discharge prevention films has a large area are locally attached, through thermal binding, to inner walls of the expansion spaces opposite to the sides at which the small area ends of the expansion agent discharge prevention films are attached so as to form filling spaces, whereby, when the expansion agent is injected through the injection spaces, the filling spaces are filled with the expansion agent, with the result that the expansion agent discharge prevention films are pressed by the expansion agent, thereby closing the injection spaces such that the expansion agent discharge prevention films come into tight contact with the inner walls of the expansion spaces to prevent discharge of the expansion agent.

5. The balloon type stent system for treatment of obesity according to claim 3, wherein the doughnut type expansion unit comprises a plurality of doughnut type expansion units communicating with one another, the doughnut type expansion units being configured to be positioned in the body of the stomach such that the obese patient feels full.

6. The balloon type stent system for treatment of obesity according to claim 5, wherein the doughnut type expansion units are configured such that diameters of the doughnut type expansion units are gradually increased from the doughnut type expansion unit connected to the cylindrical expansion unit to the outermost doughnut type expansion unit remote from the cylindrical expansion unit, whereby food digested in the stomach is easily discharged through the doughnut type expansion units.

* * * * *